(12) United States Patent
Wei

(10) Patent No.: US 8,945,050 B2
(45) Date of Patent: Feb. 3, 2015

(54) PEN NEEDLE ASSEMBLY FOR INTRADERMAL INJECTION

(75) Inventor: Min Wei, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 940 days.

(21) Appl. No.: 13/127,440

(22) PCT Filed: Nov. 6, 2009

(86) PCT No.: PCT/US2009/006020
§ 371 (c)(1),
(2), (4) Date: Jul. 28, 2011

(87) PCT Pub. No.: WO2010/053574
PCT Pub. Date: May 14, 2010

(65) Prior Publication Data
US 2011/0288526 A1 Nov. 24, 2011

Related U.S. Application Data

(60) Provisional application No. 61/193,234, filed on Nov. 7, 2008.

(51) Int. Cl.
*A61M 5/00* (2006.01)
*A61M 5/42* (2006.01)
(Continued)

(52) U.S. Cl.
CPC .............. *A61M 5/425* (2013.01); *A61M 5/46* (2013.01); *A61M 5/50* (2013.01); *A61M 2205/273* (2013.01)
USPC ........... 604/115; 604/110; 604/187; 604/192; 604/506

(58) Field of Classification Search
CPC .......................... A61M 5/425; A61M 5/3287
USPC ......... 604/115, 136–137, 156–157, 187, 192, 604/207–211, 506, 110
See application file for complete search history.

(56) References Cited

U.S. PATENT DOCUMENTS 6,743,211 B1 6/2004 Prausnitz et al.
8,409,145 B2 * 4/2013 Raymond et al. ........ 604/164.12
(Continued)

FOREIGN PATENT DOCUMENTS

JP 2005-528137 A 9/2005
WO 2004/024211 3/2004
(Continued)

OTHER PUBLICATIONS

Japanese Office Action issued in JP Patent Application No. 2011-535565 dated Nov. 5, 2013.
(Continued)

*Primary Examiner* — Theodore Stigell
(74) *Attorney, Agent, or Firm* — Roylance, Abrams, Berdo & Goodman, L.L.P.

(57) ABSTRACT

A pen needle assembly (111) includes an outer shell (151) having a first end adapted to contact a patient's skin at an injection site. A hub (131) is movably disposed within the outer shell. A needle (121) is fixed to the movable hub and has a patient end for piercing the skin at the injection site. An inner shell (171) is disposed within the outer shell and adapted to engage the pen needle assembly with a drug delivery pen (100). A first spring (141) has a first end connected to the outer shell and a second end connected to the inner shell. A second spring (161) has a first end connected to the inner shell and a second end connected to the hub. An adhesive layer (191) is disposed on the movable hub for contacting and raising the skin at the injection site.

22 Claims, 6 Drawing Sheets

(51) Int. Cl.
*A61M 5/46* (2006.01)
*A61M 5/50* (2006.01)

(56) References Cited

U.S. PATENT DOCUMENTS

| | | |
|---|---|---|
| 2003/0014018 A1 | 1/2003 | Giambattista et al. |
| 2004/0092875 A1 | 5/2004 | Kochamba |
| 2007/0021716 A1* | 1/2007 | Hansen .......................... 604/68 |
| 2007/0156096 A1 | 7/2007 | Sonoda et al. |
| 2007/0265568 A1* | 11/2007 | Tsals et al. .................... 604/136 |
| 2008/0154192 A1 | 6/2008 | Schraga |

FOREIGN PATENT DOCUMENTS

| | | |
|---|---|---|
| WO | 2004/032989 | 4/2004 |
| WO | 2007/061972 A2 | 5/2007 |

OTHER PUBLICATIONS

Supplementary European Search Report, dated Jun. 23, 2014, for EP Appln. No. 09825133.3.

* cited by examiner

PEN NEEDLE ASSEMBLY FOR INTRADERMAL INJECTION

CROSS REFERENCE TO RELATED APPLICATION

This application claims the benefit under 35 U.S.C. §119(e) of U.S. Provisional Application Ser. No. 61/193,234, filed Nov. 7, 2008, the entire disclosure of which is hereby incorporated by reference.

FIELD OF THE INVENTION

The present invention relates generally to a pen needle assembly for a drug delivery pen for intradermal medication injection. More particularly, the present invention generally relates to a pen needle assembly that facilitates intradermal medication injection. Still more particularly, the present invention provides a pen needle assembly that lifts the outer skin layer to facilitate intradermal medication injection.

BACKGROUND OF THE INVENTION

Insulin and other injectable medications are commonly given with drug delivery pens, whereby a disposable pen needle assembly is attached to facilitate drug container access and allow fluid egress from the container through the needle into the patient.

As technology and competition advance, driving the desire for shorter, thinner, less painful, and more efficacious injections, the design of the pen needle assembly and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

The assembly and operation to a typical drug delivery pen, as shown in FIGS. 1 and 2, is described in U.S. Patent Application Publication No. 2006/0229562, published on Oct. 12, 2006, which is hereby incorporated by reference in its entirety.

Drug delivery pens, such as the exemplary pen injector 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

Existing pen needle assemblies do not have means to adhere to a patient's skin during medication injection, thereby being prone to movement. Such movement can result in poor contact between the pen needle assembly and the patient's skin such that the needle is not accurately maintained in the intradermal layer during the injection. Therefore, a need exists for a pen needle assembly that provides good contact with the patient's skin to facilitate the intradermal medication injection.

Existing pen needle assemblies also do not lift the outer layer of skin (the epidermal layer) during an intradermal injection. This can result in back pressure being generated during the injection, thereby resulting in a poor injection and leaking of the medication. Additionally, by not lifting the outer skin layer, the difficulty of injecting the medication into the intradermal layer is increased. Therefore, a need exists for a pen needle assembly that lifts the outer skin layer to facilitate intradermal medication injection into the intradermal layer and to substantially prevent generation of back pressure.

Accordingly, a need exists for a pen needle assembly for a drug delivery pen that facilitates intradermal medication injection.

SUMMARY OF THE INVENTION

In accordance with an aspect of the present invention, a pen needle assembly is provided that provides improved contact with a patient's skin to facilitate intradermal medication injection.

A pen needle assembly for a drug delivery pen for intradermal medication injection transmits a desired amount of a drug solution or suspension into a patient's intradermal layer both accurately and without loss of the drug solution or suspension.

The pen needle assembly includes a user activated stamping mechanism that facilitates intradermal medication injection.

The pen needle assembly includes an adhesive layer to provide good contact between the pen needle assembly and the patient's skin, in addition to maintaining the needle in the intradermal layer during an injection.

The pen needle assembly lifts the outer layer of skin during the injection after the needle has been inserted, thereby reducing back pressure generated during the injection and substantially preventing leakage.

The pen needle assembly may include a self-locking mechanism to substantially prevent the pen needle assembly from being re-used.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

Figure 1:
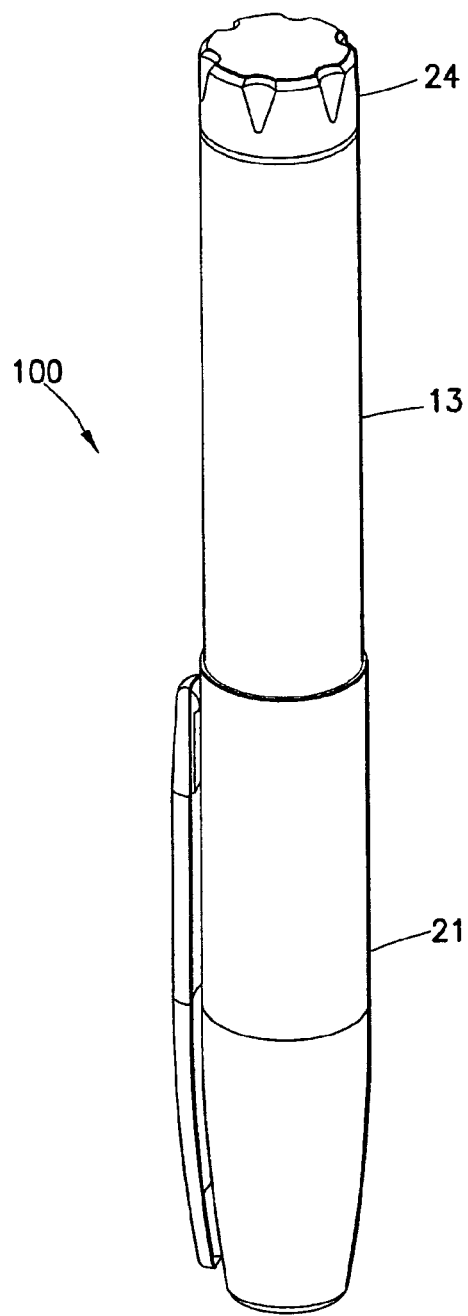
FIG. 1 is a perspective view of an assembled drug delivery pen.
Figure 2:
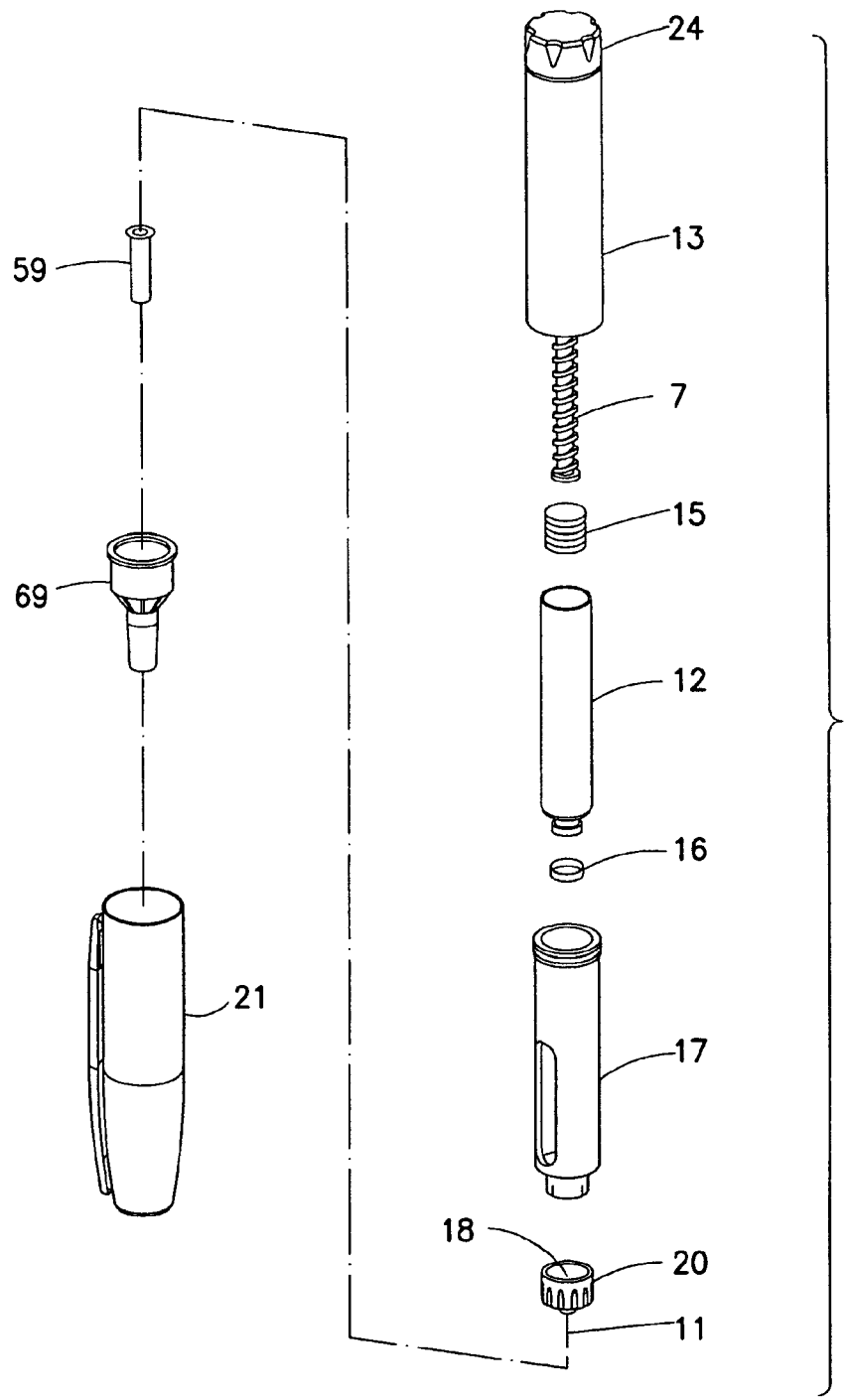
FIG. 2 is an exploded perspective view of the components of the drug delivery pen of FIG. 1.
Figure 3:
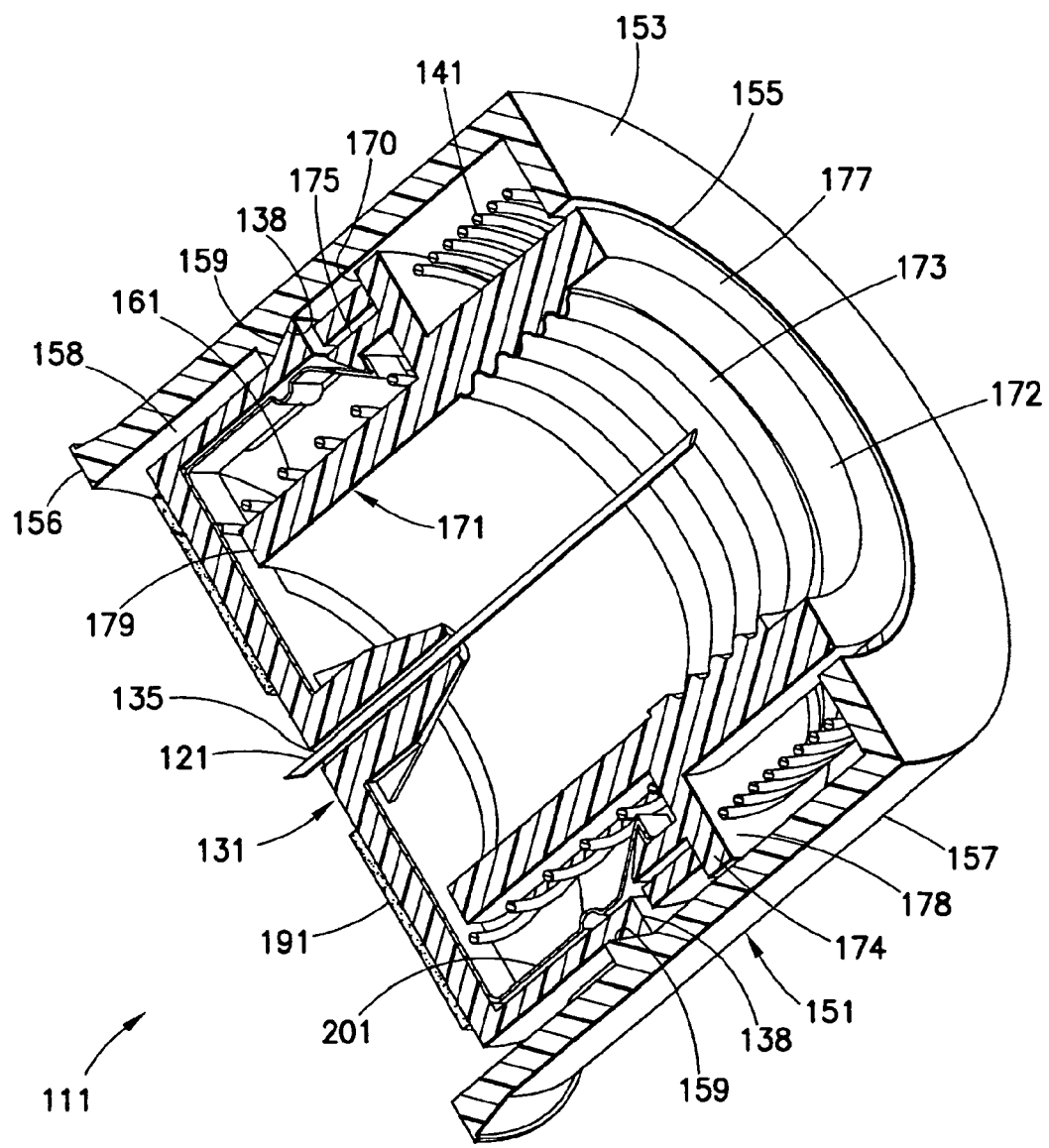
FIG. 3 is a perspective view in cross section of a pen needle assembly for a drug delivery pen for intradermal medication injection.
Figure 4:
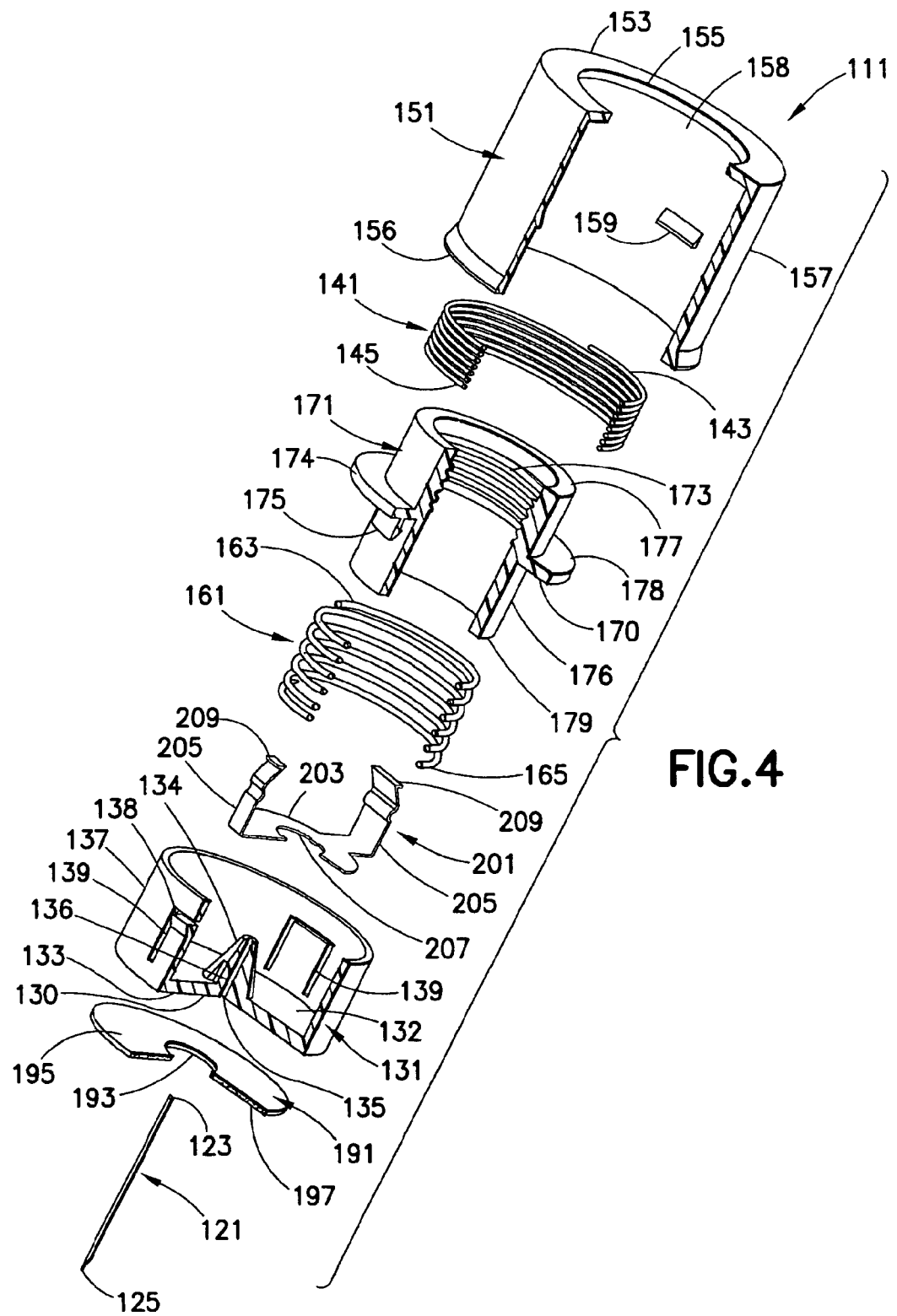
FIGS. 4-8 are elevational views in cross section illustrating operation of the pen needle assembly during an intradermal medication injection.

The following description and details of exemplary embodiments of the present invention, while generally disclosed with reference to a typical drug delivery pen, as shown in FIGS. 1 and 2, may more broadly apply to a pen needle assembly for use in conjunction with, or incorporated onto, other injection devices, such as a syringe.

Figure 5:
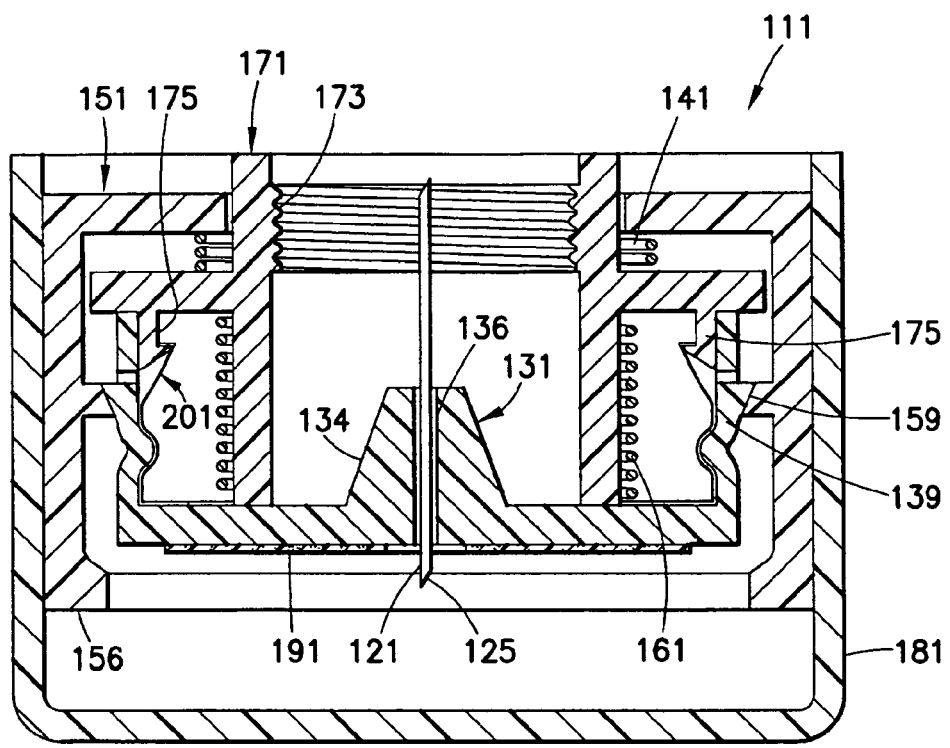

In the exemplary embodiments of the present invention shown in FIGS. 3-8, the pen needle assembly 111 includes an intradermal needle 121 fixed in a movable needle hub 131. A first end 143 of a first spring 141 is connected to an outer shell 151, and a second end 145 of the first spring is connected to an inner shell 171. A first end 163 of a second spring 161 is connected to the inner shell 171, and the second end 165 of the second spring 161 is connected to the movable needle hub 131. A safety cap 181, as shown in FIG. 5, is disposed over the needle 121.

The outer shell 151 has a base 153 with an opening 155 therein. A wall 157 extends substantially perpendicularly from the base 153. Preferably, the base 153 and the opening 155 are each substantially circular. Tabs 159 are diametrically opposed on an inner surface 158 of the wall 157 of the outer shell 151. A free end 156 of the wall 157 is adapted to engage a patient's skin at an injection site.

The inner shell 171 has a first end 177 and a second end 179 and is preferably substantially cylindrical. Threads 173 are disposed on an inner surface 172 thereof and are adapted to engage the lower housing 17 (FIG. 2). A flange 174 extends outwardly from an outer surface 176 of the inner shell. The flange 174 has an upper surface 178 and a lower surface 170. A locking prong 175 extends downwardly from a lower surface 170 of the flange 174.

The hub 131 has a base 133 with an opening 135 therein. A wall 137 extends substantially perpendicularly from the base 133. Preferably, the base 133 and the opening 135 are each substantially circular. Flexible actuators 139 are formed in the wall 137 and are diametrically opposed. A projection 138 is formed at the free end of each actuator 139. The projections 138 are adapted to engage the tabs 159 of the outer shell 151 prior to an injection. A protrusion 134 extends upwardly from an inner surface 132 of the base 133. A passageway 136 extends through the entirety of the protrusion 134 to the opening 135 in the base 133 of the hub 131.

A retaining latch 201 has a base 203 and diametrically opposed arms 205 extending upwardly therefrom. The base has an opening 207 adapted to receive the hub protrusion 134. A hook 209 is formed at the free end of each of the arms 205. The hooks are adapted to engage the locking prongs 175 of the inner shell 171 prior to an injection.

An upper surface 195 of the adhesive layer 191 is secured to a lower surface 130 of the hub base 133. Preferably, the adhesive layer is substantially circular and corresponds to the shape of the hub base 133. An opening 193 in the adhesive layer 191 is aligned with the opening 135 in the hub base 133. A lower surface 197 of the adhesive layer 191 is adapted to contact a patient's skin at the injection site during an injection.

A first spring 141 is disposed between the outer shell 151 and the inner shell 171. A first end 143 of the first spring 141 is connected to the base 153 of the outer shell 171 and a second end 145 of the first spring 141 is connected to the upper surface 178 of the flange 174 of the inner shell 171.

A second spring 161 is disposed between the inner shell 171 and the hub 131. A first end 163 of the second spring 161 is connected to the lower surface 170 of the flange 174 of the inner shell 171 and a second end 165 of the second spring 161 is connected to the upper surface 132 of the hub base 133.

A needle 121 is received by the passageway 136 in the hub protrusion 134. The needle 121 has a non-patient end 123 that is adapted to pierce the cartridge septum 16 (FIG. 2) and a patient end 125 that passes through the opening 135 in the hub base 133 and is adapted to pierce a patient's skin at the injection site during an injection.

An assembled pen needle assembly 111 is shown in FIG. 5. The threads 173 of the inner shell receive a threaded portion of the lower housing 17 (FIG. 2), which is not shown in FIGS. 5-8 for clarity. A safety cap 181 is disposed over the outer shell 151 and is secured thereto in any suitable manner, such as an interference fit. The safety cap 181 prevents an accidental needle stick. Prior to an injection, the first spring 141 between the outer shell 151 and the inner shell 171 is in a relaxed position. The second spring 161 between the inner shell 171 and the hub 131 is in a compressed position. The hook 209 of the retaining latch 201 receives the locking prong 175 of the inner shell 171, thereby preventing movement of the inner shell. The hub projections 138 engage the tabs 159 of the outer shell 151, thereby preventing movement of the hub 131 and outer shell.

Figure 6:
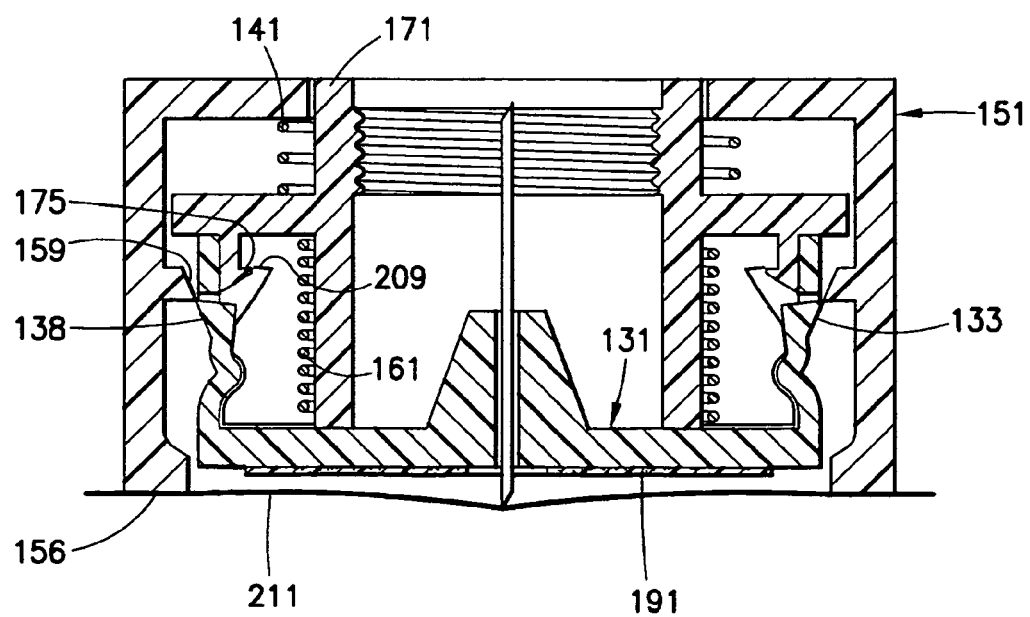

To perform an intradermal medication injection, the safety cap 181 is removed. The drug delivery pen is pushed against the patient's skin 211 such that the free end 156 of the outer shell 151 contacts the patient's skin. The outer shell 151 is moved upwardly (away from the patient's skin 211) along a longitudinal axis, as shown in FIG. 6. This movement of the outer shell 151 causes the hub projections 138 to flex and move radially inwardly, thereby unlocking the locking mechanism between the retaining latch hook 209 and the locking prong 175.

Figure 7:
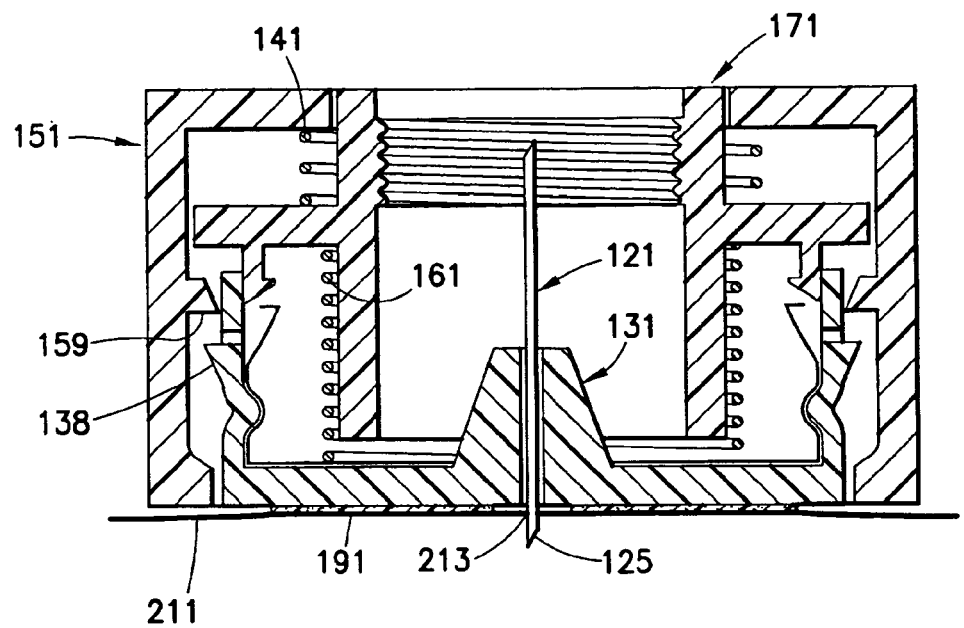

As shown in FIG. 7, when the latch hook 209 and the locking prong 175 disengage, the second spring 161 is able to uncompress and extend. This movement of the second spring 161 urges the movable hub 131 and the needle 121 downwardly, thereby inserting the needle 121 into an intradermal layer of the patient's skin 211 at the injection site 213. This movement also causes the first spring 141 to become stretched. The adhesive layer 191 on the needle hub 131 adheres onto an outer layer of the patient's skin 211. The second spring 161 is then in either a relaxed or slightly compressed position.

Figure 8:
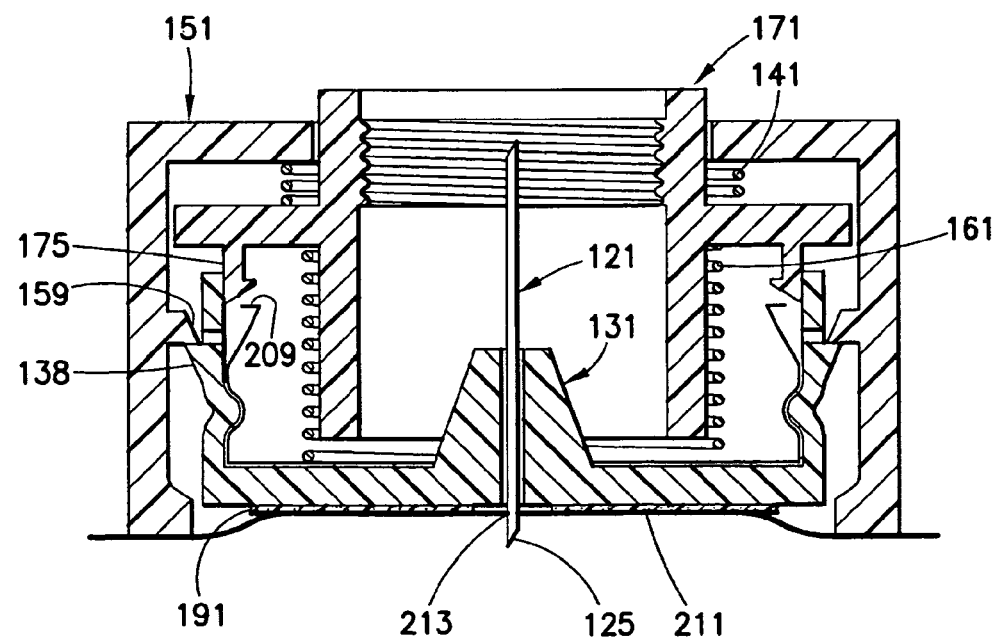

As shown in FIG. 8, the pushing force on the drug delivery pen is released. Releasing such force on the inner shell, causes the first spring 141 to return to its original position, thereby lifting the inner shell 171, the needle hub 131 and the patient's skin 211 adhered to the adhesive layer 191 upwardly. The retraction of the needle hub 131 lifts the adhered outer skin layer, thereby creating space in the intradermal layer to facilitate the intradermal medication injection. After the injection is complete, the pen needle assembly 111 is detached from the drug delivery pen 100 (FIGS. 1 and 2) and is properly disposed of.

Preferably, the hub projections 138 and the outer shell tabs 159 have sloped surfaces, as shown in FIG. 8. Such sloped prevent upward movement of the hub 131, such that the pen needle assembly 111 cannot be re-used. Because the hub 131 cannot be moved past the projections 159, the second spring 161 cannot be recompressed to drive another needle insertion.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A pen needle assembly, comprising:
an outer shell having a first end configured to engage the skin of a patient and a second end;
an inner shell disposed within said outer shell and engageable with a drug delivery device, said inner shell being slidable within said outer shell and having a first end and a second end,
a hub movably disposed within said outer shell and being movable relative to said outer shell and inner shell;
a needle rigidly fixed to said hub;
an adhesive layer disposed on said hub;
a first spring coupled to said outer shell and to said inner shell to retract said inner shell toward said second end of said outer shell;
a second spring extending between said inner shell and hub to bias said hub away from said first end of said inner shell;
wherein said hub and inner shell move downwardly relative to said outer shell during an injection to adhere said adhesive layer on a patient's skin and move upwardly relative to said outer shell to raise the patient's skin to facilitate the injection.

2. A pen needle assembly according to claim 1, wherein a tab disposed on an inner surface of said outer shell engages a projection disposed on said hub, thereby preventing upward movement of said hub after an injection such that the pen needle assembly cannot be re-used.

3. A pen needle assembly according to claim 1, further comprising
a safety cap removably connected to said outer shell.

4. A pen needle assembly according to claim 1, wherein said inner shell has an outwardly extending flange with a top face and a bottom face, said first spring being connected to said top face and to said outer shell, and said second spring has a first end contacting said bottom face and a second end contacting said hub.

5. The pen needle assembly according to claim 4, further comprising
a latch hook having one end coupled to said hub, and a second end with a hook engaging a prong on said inner shell, said second spring biasing said hub away from said inner shell when said hook disengages from said prong.

6. The pen needle assembly according to claim 5, wherein said prong extends from said bottom face of said flange toward said hub, and where said outer shell and inwardly extending tab coupled to an outwardly extending protrusion on said hub, and where downward movement of said inner shell contacts said hub to disengage said tab with said prong whereby said second spring biases said hub away from said inner shell.

7. A pen needle assembly, comprising:
an outer shell having a first end adapted to engage a patient's skin at an injection site;
a hub movably disposed within said outer shell;
a needle fixed to said hub and having a patient end for piercing the skin at the injection site;
an inner shell disposed within said outer shell and engageable with a drug delivery pen, said hub being movable relative to the inner shell;
a first spring having a first end connected to said outer shell and a second end connected to said inner shell;
a second spring having a first end connected to said inner shell and a second end connected to said hub;
an adhesive layer disposed on said movable hub for contacting and raising the skin at the injection site; and
a retaining latch disposed between said hub and said inner shell to prevent movement of said hub relative to said inner shell when said retaining latch is engaged with said inner shell.

8. A pen needle assembly according to claim 7, further comprising
a safety cap removably connected to said outer shell and covering said patient end of said needle.

9. A pen needle assembly according to claim 7, wherein said inner shell has a locking prong engaged by said retaining latch.

10. A pen needle assembly according to claim 7, wherein a projection on said hub engages a tab on said outer shell, thereby preventing upward movement of said hub after an injection such that the pen needle assembly cannot be re-used.

11. A pen needle assembly according to claim 7, wherein said first spring is not compressed between said outer shell and said inner shell when said retaining latch is engaged with said inner shell.

12. A pen needle assembly according to claim 7, wherein said second spring is compressed between said inner shell and said hub when said retaining latch is engaged with said inner shell.

13. A drug delivery pen, comprising:
a medicament cartridge;
an outer shell having a first end adapted to engage a patient's skin at an injection site;
a hub movably disposed within said outer shell;
a needle fixed to said movable hub and having a patient end for piercing the skin at the injection site;
an inner shell disposed within said outer shell and adapted to engage said a lower housing of the drug delivery pen;
a first spring having a first end connected to said outer shell and a second end connected to said inner shell to retract said inner shell and hub with respect to said outer shell;

a second spring having a first end connected to said inner shell and a second end connected to said hub to bias said hub away from said inner shell; and an adhesive layer disposed on said movable hub for contacting and raising the skin at the injection site.

14. A drug delivery pen according to claim 13, further comprising a safety cap removably connected to said outer shell and covering said patient end of said needle.

15. A drug delivery pen according to claim 13, wherein a retaining latch disposed between said hub and said inner shell prevents movement of said hub relative to said inner shell when said retaining latch is engaged with said inner shell.

16. A drug delivery pen according to claim 15, wherein said inner shell has a locking prong engaged by said retaining latch.

17. A drug delivery pen according to claim 13, wherein a projection on said hub engages a tab on said outer shell, thereby preventing upward movement of said hub after an injection such that the pen needle assembly cannot be re-used.

18. A method of facilitating medicament injection, comprising the steps of:

moving an outer shell of a pen needle assembly upwardly relative to an inner shell and a needle hub by pushing downwardly on a pen needle assembly on a patient's skin at an injection site;

flexing a projection of the hub of the pen needle assembly inwardly responsive to the upward movement of the outer shell to unlock the hub from the inner shell;

moving the hub downwardly responsive to the unlocking of the hub relative to the inner shell and outer shell to contact an adhesive layer disposed on the hub with the patient's skin at the injection site; and retracting the inner shell and hub relative to the outer shell and raising the skin at the injection site upwardly, thereby facilitating the injection.

19. A method of facilitating medicament injection according to claim 18, further comprising moving the hub downwardly with respect to the outer shell and inner shell by a spring disposed between the inner shell and the hub to bias the hub away from the inner shell.

20. A method of facilitating medicament injection according to claim 18, further comprising moving the hub and inner shell upwardly with respect to the outer shell by a spring disposed between the inner shell and the outer shell to retract the inner shell and hub with respect to the outer shell.

21. A method of facilitating medicament injection according to claim 18, wherein flexing the projection inwardly disengages a latching hook from a locking prong on the inner shell to allow movement of the hub relative to the inner shell.

22. A method of facilitating medicament injection according to claim 18, further comprising limiting upward movement of the hub relative to the outer shell to prevent re-use of the pen needle assembly after an injection.

\* \* \* \* \*